United States Patent [19]

Bjorklund

[11] 4,137,129

[45] Jan. 30, 1979

[54] FRACTIONATION PROCESS

[75] Inventor: Bradford L. Bjorklund, Mt. Prospect, Ill.

[73] Assignee: UOP Inc., Des Plaines, Ill.

[21] Appl. No.: 840,346

[22] Filed: Oct. 7, 1977

[51] Int. Cl.² .......................... C07C 7/04; B01D 1/28; B01D 3/06

[52] U.S. Cl. ........................ 203/26; 203/78; 203/88; 62/26; 62/31; 260/676 R; 260/677 A

[58] Field of Search ....................... 203/26, 24, 88, 73, 203/78, DIG. 4; 62/24-28, 30, 31; 260/677 A, 676 R

[56] References Cited

U.S. PATENT DOCUMENTS

| | | | |
|---|---|---|---|
| 2,127,004 | 8/1938 | Nelson | 203/DIG. 4 |
| 3,260,057 | 7/1966 | Becker | 260/677 A |
| 3,414,484 | 12/1968 | Carson et al. | 203/26 |
| 3,418,215 | 12/1968 | Nirenberg | 203/26 |
| 3,568,457 | 3/1971 | Briggs et al. | 62/26 |
| 3,654,094 | 4/1972 | Yamagishi et al. | 203/26 |

Primary Examiner—Wilbur L. Bascomb, Jr.
Attorney, Agent, or Firm—James R. Hoatson, Jr.; John F. Spears, Jr.; William H. Page, II

[57] ABSTRACT

A process for separating two close-boiling chemical compounds by fractionation wherein the bottoms liquid stream removed from the fractionation column is flashed to produce cool liquid which is then used to condense overhead vapors of the column. The column is reboiled by vapor derived from the flashed bottoms liquid stream and which has been heated by compression in a heat pump.

18 Claims, 1 Drawing Figure

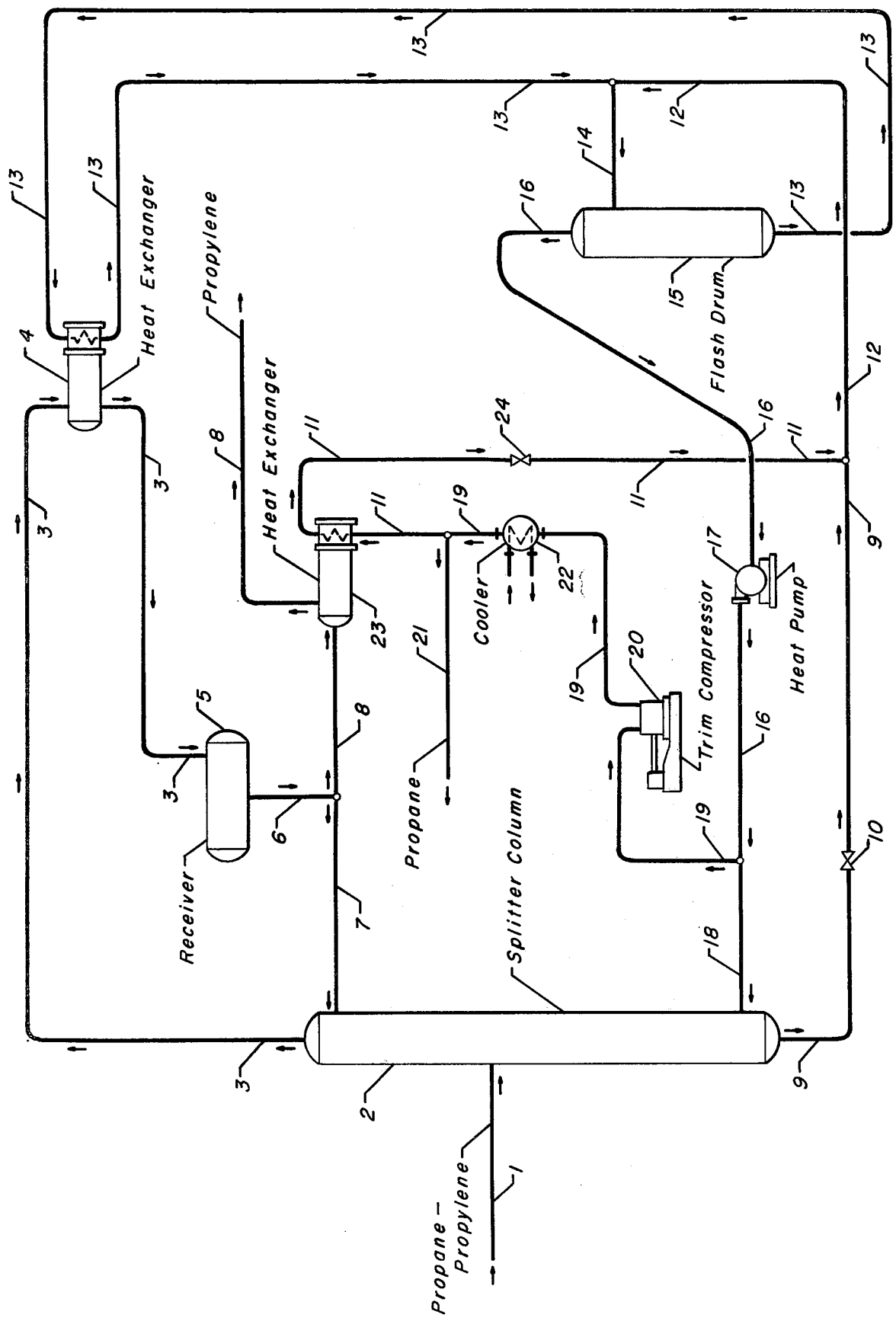

FRACTIONATION PROCESS

FIELD OF THE INVENTION

The invention relates to a process for separating two close-boiling chemical compounds by fractionation. The invention more specifically relates to a process for fractionating a mixture of two close-boiling hydrocarbons. The invention also relates to the use of heat pumps in the fractionation of hydrocarbons. References concerned with similar subject matter are found, for instance, in Classes 55, 62 and 203.

PRIOR ART

The separation of hydrocarbons by fractionation is an old and well developed art. Those skilled in the art have recognized that in certain situations heat pumps may be used to advantage to reduce the utilities cost of operating a fractionation process. This recognition has led to the utilization of a heat pump to reboil the bottom of a fractionation column by the indirect heat exchange of bottoms liquid and compressed overhead vapors of the same column. Separatory processes utilizing this are presented in U.S. Pat. Nos. 3,230,155 and 3,414,484 (both Cl. 203-26). A similar system in which a separate refrigerant liquid is used to transfer heat removed in condensing the overhead vapors to the reboiled liquid is shown in U.S. Pat. No. 2,534,274.

The conventional or prior art method of utilizing a heat pump in a fractionation process is also described in some detail in the article starting at page 85 of the Sept. 1, 1975 edition of the *Oil and Gas Journal*. The article is directed to the use of heat pumps in conjunction with other aids, such as enhanced heat transfer reboiler tubing and high liquid loading trays, to conserve energy normally expended in the fractionation of close-boiling compounds. The article also presents a high efficiency system in which a trim compressor and trim condenser are used to remove heat from a previously compressed portion of the overhead vapor. Specific examples of the use of the process are the separation of propylene and propane; butene-2 and isobutane; and ethylene and ethane. It is believed these references adequately set out the main features of the prior art use of heat pumps in fractionation processes.

In these prior art systems the overhead vapor is compressed to raise its temperature and is then passed into the reboiler located at the bottom of the column. The indirect heat exchange in the reboiler causes the condensation of at least some of the overhead vapor to produce overhead liquid. This liquid is used as reflux and removed as a product. The heat exchange also vaporizes a portion of the bottoms liquid to reboil the column.

The subject process is different from these prior art systems in several ways. For instance, in the subject process there is no heat exchanger used as a reboiler. Instead vapors which have been heated in the heat pump are passed directly into the column. This adds the required heat to the bottom of the column. A second distinguishing feature of the subject process is that the bottoms liquid removed from the column is flashed to a lower pressure and temperature. This produces liquid which is colder than the overhead vapors of the column and which is used to condense the overhead vapors. It is believed that the prior art processes do not perform this flashing operation, do not produce an equivalent cold liquid and do not condense the overhead vapor in a similar manner.

BRIEF SUMMARY OF THE INVENTION

The invention provides an energy efficient process for separating two close-boiling chemical compounds by fractionation. This process may be broadly characterized as comprising the steps of passing a feed stream comprising a first and a second chemical compound into a fractionation zone; removing an overhead vapor stream comprising the first chemical compound from the fractionation zone and at least partially condensing the overhead vapor stream by indirect heat exchange to form overhead liquid used to form reflux and product streams; removing a bottoms stream comprising the second chemical compound from the fractionation zone and flashing the bottoms liquid stream to produce a mixed-phase stream having a lower pressure and a lower temperature than the bottoms liquid stream; heat exchanging a liquid-phase portion of the mixed-phase stream against the overhead vapor stream to effect the previously described condensation; compressing a working vapor stream which comprises vapor formed in flashing the bottoms liquid stream to form a high pressure stream having a higher pressure and temperature than the bottoms liquid stream; and passing at least a portion of the high pressure vapor stream into the fractionation zone to effect the reboiling of the fractionation zone.

In another embodiment of the invention the bottoms liquid stream is flashed under conditions which produce only a cold vapor stream. All or only a portion of this vapor stream is used as the refrigerant stream used to condense the overhead vapors.

DESCRIPTION OF THE DRAWING

The Drawing illustrates the preferred embodiment of the invention. For clarity and simplicity various subsystems and apparatus associated with the operation of the process have not been shown. These items include flow and pressure control systems, pumps, temperature and pressure monitoring systems, fractionator internals, valves, etc., which may be of customary design and manufacture. This representation of the preferred embodiment is not intended to preclude from the scope of the invention those other embodiments set out herein or which are the result of reasonable and normal modification of these embodiments.

Referring now to the Drawing, a feed stream which is a substantially pure mixture of propane and propylene is fed into an intermediate point of a fractionation column 2 through line 1. This column is operated at fractionation conditions which result in the feed stream being separated into overhead vapors of substantially pure propylene and bottoms liquid of substantially pure propane. The overhead vapor stream is removed in line 3 and condensed in a heat exchanger 4. The resulting overhead liquid is collected in the overhead receiver 5. It is withdrawn through line 6 and divided into the reflux stream carried by line 7 and the propylene product stream carried by line 8.

The bottoms liquid stream is removed from the column in line 9 and flashed to a lower pressure and temperature at the control valve 10. The resulting mixed-phase stream is admixed with the vapor stream carried by line 11 and passed through line 12. The mixed-phase contents of line 12 are then admixed with a mixed-phase stream from line 13 and passed into a flash drum 15 via line 14. The bottoms liquid stream and the streams mixed with it are all substantially pure propane. The flash drum is a vapor-liquid phase separation zone wherein the entering material is separated into a liquid-phase refrigerant stream carried by line 13 and a vapor-phase working stream withdrawn through line 16. The refrigerant stream is passed through the heat exchanger 4 to effect the condensation of the overhead vapor stream. The heat picked up by the refrigerant stream vaporizes at least a portion of the refrigerant stream, thereby forming the mixed-phase stream which is recycled to the flash drum.

The working vapor stream removed from the flash drum in line 16 is pressurized in a heat pump 17. This raises the temperature of the working stream above that of the bottoms liquid stream. A major portion of the now superheated working stream is passed into the bottom of the fractionation column through line 18 to reboil the column. A second portion of the heated working vapor stream is diverted into line 19 and passed into a trim compressor 20. This further heats the second portion of the working stream. This portion of the working vapor is then cooled in exchanger 22 to maintain the heat balance within the system. A part of this vapor stream is removed as the propane product stream through line 21. The remaining part of the second portion of the working stream is carried through the indirect heat exchanger 23 by line 11. This second heat exchange operation further cools the material in line 11, with the second exchange using the overhead liquid product stream as the coolant. The portion of the working stream in line 11 is then depressurized at valve 24 and admixed into the flashed bottoms stream for recycling to the flash drum.

DETAILED DESCRIPTION

The constantly increasing cost of energy has prompted renewed emphasis on the development of energy-efficient petroleum and petrochemical processes. One of the common energy-consuming operations in many of these processes is the separation of two chemical compounds by fractionation. It is an objective of this invention to provide a highly energy-efficient fractionation process for such separations. It is another objective of the invention to provide a fractionation process for the separation of close-boiling chemical compounds using a heat pump. It is yet another objective of the invention to provide an energy-efficient process for separating hydrocarbons having the same number of carbon atoms per molecule by fractionation.

The subject process may be applied to any fractionation process in which the use of a heat pump is practical. The chemical compounds in the feed stream may comprise inorganic chemicals, inorganically substituted organic chemicals or hydrocarbons. The feed stream may therefore comprise halogenated hydrocarbons, alcohols, ethers, ketones, olefins, paraffins or aromatics. The use of a heat pump on a fractionation column is normally restricted to use with relatively close-boiling compounds. The compounds to be separated therefore preferably have boiling points which are no more than 20 Fahrenheit degrees apart at the pressure imposed in the fractionation column. A better statement of this criteria is that the separation of the two compounds is difficult due to the vapor-liquid equilibrium ratios or K's of the two compounds being close to the same value, or that $\alpha$, the relative volatility of the system, is close to unity. This situation indicates the need for a high reflux ratio and results in high utility costs for the separation.

The subject process utilizes a heat pump. These devices function by compressing a vapor stream, an action which in accordance with the laws of thermodynamics increases the temperature of the vapor stream. The vapor stream may then be heat exchanged against an object which it is desired to heat. The effect of the heat pump is to establish a thermal gradient which allows practical heat transfer at the expense of mechanical energy. Heat pumps therefore allow heat to be added to or removed from a system by the application of mechanical energy to a circulating working stream. In some situations the use of heat pumps is more energy-efficient than other methods. This has been recognized in the art as shown by the increased usage and attention being given to heat pumps in such diverse areas as fractionation and residential air conditioning and heating.

Heat pumps have been used in what is referred to herein as the conventional manner to improve the energy-efficiency of fractionation systems. The previously cited prior art illustrates these conventional heat pump systems in which warm overhead vapors are compressed and thereby heated to a temperature sufficient for use in the reboiler system. The hot vapors are then indirectly heat exchanged with the bottoms liquid to be vaporized. Typically the hot overhead vapor stream is simultaneously condensed to form a liquid used as reflux and withdrawn as the overhead product.

In the subject process the overhead vapor stream is not compressed, and the bottom liquid is not heated by indirect heat exchange as in the conventional heat pump system. Instead, the bottoms liquid is flashed to a lower pressure which causes the formation of a relatively cold fluid stream. This fluid stream is preferably a mixed-phase stream but may be a cold vapor-phase stream. Preferably, the bottoms liquid is substantially pure, and the composition of the vapor and liquid phases produced by the flashing operation are the same or similar. At least a portion of the resultant cold liquid or vapor is then used as a refrigerant and heat exchanged against the overhead vapor stream of the column. This causes the condensation of overhead vapor and the vaporization of at least a portion of the cold liquid. The vapors formed in this heat exchange step and in the vapors formed in flashing the bottoms liquid are combined to form a vapor stream, at least a portion of which is fed to the heat pump. The effluent of the heat pump is a superheated vapor stream which is passed into the bottom of the column to effect the reboiling of the column.

The following example, which is based on a proposed commercial installation, illustrates the use of the subject process. It is based on a system similar to that shown in the drawing, and reference will occasionally be made to the numerals used in the drawing to clarify the particular stream or apparatus being described. The feed stream to the column is a mixed-phase mixture of propane and propylene having a flow rate of about 727 mph (moles per hour). It enters at an intermediate point of the 166 tray column, preferably at the 77th tray from the top of the column. An overhead vapor stream having a flow rate of about 8420 mph leaves the column at a pressure of about 75 psig. and a temperature of about 36° F. The overhead vapor stream is condensed in heat exchanger 4 and the resultant overhead liquid enters the overhead receiver at a temperature close to 34° F. About 800 mph of the overhead liquid is removed in line 8 as a substantially pure propylene product stream.

A bottoms liquid stream having a temperature of about 58° F. and a pressure close to 92 psig. is removed from the bottom of the column. This stream is flashed to a pressure of approximately 42 psig. at valve 10, thereby forming a vapor-phase and a liquid-phase. Both of these phases are substantially pure propylene, and they are passed through lines 9, 12 and 14 to a flash drum. Vapor from several sources also enters this drum to be separated from any liquid with which it may be admixed. The vapor phase is removed at the rate of approximately 10,700 mph, and the liquid phase is removed as a refrigerant stream at the rate of about 8,740 mph in line 13. Both of these streams have a temperature of approximately 20° F. and a pressure of about 42 psig. The flow rates of these two streams are high due to the internal recycling of various streams, such as compressor spillback streams, to the flash drum.

The liquid phase refrigerant stream which is removed from the flash drum is passed into the heat exchanger 4 used as an overhead condenser. A plate-type heat exchanger is preferred. About 7,960 mph of this refrigerant stream is vaporized by this heat exchange, and the resultant mixed-phase stream is returned to the flash drum at a temperature of about 20° F. The vapor-phase removed from the flash drum, which is referred to herein as a working stream, is passed into the heat pump 17 and compressed to about 92 psig. The vapor-phase effluent of the heat pump has a temperature of approximately 78° F. A first portion of this superheated working stream is passed into the bottom of the fractionation column 2 at the rate of about 7,800 mph. the total working stream may in some cases be passed into the column.

To maintain the system on which this particular example is based in heat balance, a 1665 mph second portion of the heated working stream is passed through line 19 for heat exchange. It is first heated in a trim compressor to a temperature which allows heat rejection to a normal cooling medium such as moderator temperature water. The effluent of the trim compressor has a temperature of about 131° F. and a pressure of approximately 167 psig. This heated vapor is cooled to about 95° F. in the trim condenser or cooler 22. A net bottoms stream is removed as the product stream in line 21 at the rate of about 280 mph. It is substantially pure propane. The remaining material is cooled to approximately 67° F. in cooler 23 by heat exchange against the propylene product stream and is then returned to the flash drum after being depressurized through the control valve 24.

In accordance with this description, the invention may be characterized as a process for separating two hydrocarbons by fractionation which comprises the steps of passing a feed stream comprising a first and a second hydrocarbon into an intermediate point of a fractionation column operated at fractionation conditions which include a first pressure; removing an overhead vapor stream which is rich in the first hydrocarbon from the fractionation column, at least partially condensing the overhead vapor stream by indirect heat exchange to produce an overhead liquid, supplying a portion of the overhead liquid to the fractionation column as reflux and removing a second portion as a first product stream; removing a bottoms liquid stream, which is substantially pure stream of the second hydrocarbon, from the fractionation column, and flashing the bottoms liquid stream to produce a mixed-phase stream having a lower temperature than the bottoms liquid stream; passing the mixed-phase stream into a vapor-liquid phase separation zone; removing a liquid-phase refrigerant stream from the phase separation zone and heat exchanging the refrigerant stream against the overhead vapor stream to effect the previously described condensation; returning the refrigerant stream to the vapor-liquid phase separation zone; removing a vapor-phase working stream from the phase separation zone, and heating the working stream by compression to a first temperature above that of the bottoms liquid stream; and, passing at least a first portion of the working stream into the bottom of the fractionation column to effect the reboiling of the fractionation column.

Any reference herein to a stream as being rich in a particular compound is intended to indicate that over 90 mol.% of the stream is made up of the particular compound. In a similar manner referring to a stream as substantially pure is intended to indicate it contains over 99 mol.% of the indicated compound. These relative terms are necessary because of the minor amounts of contaminants which are commonly found in industrial grade chemical streams. This is in keeping with the common knowledge of those skilled in the art that it is often commercially impractical to utilize or produce process streams which are pure in the true sense of the word. Nevertheless, it is preferred that both the overhead and bottoms stream be substantially pure streams of a single compound.

The subject process may be used with flow schemes which differ from that shown in the Drawing. For instance, it may not be necessary to utilize the trim compressor and trim cooler to remove heat from the system. It may in other situations not be desirable to heat exchange the overhead product stream against a portion of the heated working vapor stream. Another area of variation is the point at which the bottoms product stream is removed. This product stream may be a liquid-phase stream removed from the bottom of the column or from the flash drum. The bottoms product stream may also be a part of the vapor fraction formed by flashing the bottoms liquid stream. In this case only a portion of the vapor fraction is compressed as the working vapor stream.

The process flow may also be varied by having each stream which is eventually returned to the flash drum carried by a separate line. It is also possible to pass the various mixed-phase streams into two or more different vapor-liquid separators rather than into a single vessel. Another possible variation is the depressurization of the bottoms stream and any recycled portion of the working stream through an energy recovery means such as a turbine. The energy recovered in this manner could be used for compressing vapor streams or pumping the product or refrigerant streams.

The previously described flashing of the bottoms stream to produce only a cold vapor-phase stream is another possible variation from the preferred embodiment. In this embodiment of the invention the vapor-liquid separation zone could be eliminated if desired. However, some form of similar apparatus seems prudent to remove residual liquid upstream of the primary heat pump. A mixed-phase stream is the preferred result of the flashing step for control purposes. Except for changes to the process due to the presence of only a vapor-phase, this embodiment of the process would be practiced in a manner similar to the preferred embodiments just described.

The apparatus and the conditions necessary to practice the invention may be of customary design, and their specification is within the expertise of those skilled in the art.

The subject invention is believed to be more economical for the fractionation of $C_3$ hydrocarbons than a conventional heat pump system. This is due to reduced horsepower requirements for the heat pump. Other advantages of the subject process over conventional heat pumps include the use of a pumped refrigerant, which provides greater flexibility, and the ease of startup of the system. The easier startup results from the process's ability to produce overhead refrigerant liquid by simply flashing a portion of the liquid pumped into the fractionation column. In comparison the prior art systems require the operation of the compressor used as the heat pump before the overhead vapors may be condensed.

I claim as my invention:

1. A process for separating two chemical compounds by fractionation which comprises the steps of:
    (a) passing a feed stream comprising a first and a second chemical compound into a fractionation zone operated at fractionation conditions;
    (b) removing an overhead vapor stream which is rich in the first chemical compound from the fractionation zone, at least partially condensing the overhead vapor stream by indirect heat exchange to produce overhead liquid, supplying a portion of the overhead liquid to the fractionation zone as reflux and removing a portion of the overhead liquid as a first product stream;
    (c) removing a bottom liquid stream which is rich in the second chemical compound from the fractionation zone and flashing the bottoms liquid stream to produce a mixed-phase stream having a lower pressure and temperature than the bottoms liquid stream;
    (d) dividing the mixed-phase stream into a liquid fraction and a vapor fraction;
    (e) heat exchanging at least a portion of the liquid fraction against the overhead vapor stream to effect the previously described condensation of the overhead vapor stream;
    (f) compressing a working vapor stream, which comprises at least a first portion of the vapor fraction of the mixed-phase stream, to form a high pressure vapor stream having a higher temperature than the bottoms liquid stream; and,
    (g) passing at least a portion of the high pressure vapor stream into the fractionation zone to effect the reboiling of the fractionation zone.

2. The process of claim 1 wherein a second portion of the vapor fraction of the mixed-phase stream is removed as a second product stream.

3. The process of claim 1 wherein a second portion of the high pressure vapor stream is removed as a second product stream.

4. The process of claim 1 wherein the overhead vapor stream and the bottoms liquid stream are substantially pure streams.

5. The process of claim 4 wherein the boiling points of the first and the second chemical compounds are no more than 20 Fahrenheit degrees apart at the pressure imposed in the fractionation column.

6. The process of claim 4 wherein the first and the second chemical compounds are hydrocarbons having the same number of carbon atoms per molecule.

7. The process of claim 6 wherein the first and the second chemical compounds have fewer than six carbon atoms per molecule.

8. A process for separating two hydrocarbons by fractionation which comprises the steps of:
    (a) passing a feed stream comprising a first and a second hydrocarbon into an intermediate point of a fractionation column operated at fractionation conditions which include a first pressure;
    (b) removing an overhead vapor stream which is rich in the first hydrocarbon from the fractionation column, at least partially condensing the overhead vapor stream by indirect heat exchange to produce an overhead liquid, supplying a portion of the overhead liquid to the fractionation column as reflux and removing a second portion as a first product stream;
    (c) removing a bottoms liquid stream, which is a substantially pure stream of the second hydrocarbon, from the fractionation column, and flashing the bottoms liquid stream to produce a mixed-phase stream having a lower temperature than the bottoms liquid stream;
    (d) passing the mixed-phase stream into a vapor-liquid phase separation zone;
    (e) removing a refrigerant stream from the vapor-liquid phase separation zone and heat exchanging the refrigerant stream against the overhead vapor stream to effect the previously described condensation;
    (f) returning the refrigerant stream to the vapor-liquid phase separation zone;
    (g) removing a vapor-phase working stream from the phase separation zone, and heating the working stream by compression to a first temperature above that of the bottoms liquid stream; and,
    (h) passing at least a first portion of the working stream into the bottom of the fractionation column to effect the reboiling of the fractionation column.

9. The process of claim 8 wherein (a) a second portion of the working stream is further heated by compression to a second temperature which is higher than said first temperature; and, (b) at least a first part of the thus-heated second portion of the working stream is cooled by indirect heat exchange, depressurized and returned to the vapor-liquid phase separation zone.

10. The process of claim 9 wherein a second part of the heated second portion of the working stream is removed from the process as a second product stream.

11. The process of claim 8 wherein the entire working stream is passed into the bottom of the fractionation column.

12. The process of claim 8 wherein the first and the second hydrocarbon together comprise over 99 mol.% of the feed stream.

13. The process of claim 12 wherein the overhead vapor stream is a substantially pure stream of the first hydrocarbon.

14. The process of claim 13 wherein the first and the second hydrocarbon have the same number of carbon atoms per molecule.

15. The process of claim 14 wherein the first hydrocarbon has less than six carbon atoms per molecule.

16. The process of claim 13 wherein the bottoms liquid stream is depressurized through an energy recovery means.

17. The process of claim 9 wherein the refrigerant stream is a liquid when removed from the vapor-liquid phase separation zone.

18. A process for separating two chemical compounds by fractionation which comprises the steps of:
(a) passing a feed stream comprising a first and a second chemical compound into a fractionation zone operated at fractionation conditions;
(b) removing an overhead vapor stream which is rich in the first chemical compound from the fractionation zone, at least partially condensing the overhead vapor stream by indirect heat exchange to produce overhead liquid, supplying a portion of the overhead liquid to the fractionation zone as reflux and removing a portion of the overhead liquid as a first product stream;
(c) removing a bottoms liquid stream which is rich in the second chemical compound from the fractionation zone and flashing the bottoms liquid stream to produce a cold vapor stream having a lower pressure and temperature than the bottoms liquid stream;
(d) heat exchanging at least a portion of the cold vapor stream against the overhead vapor stream to effect the previously described condensation of the overhead vapor stream;
(e) heating a working vapor stream, which comprises at least a portion of the cold vapor stream, by compression in a heat pump to a higher temperature than the bottoms liquid stream; and,
(f) passing at least a portion of the working vapor stream into the fractionation zone to effect the reboiling of the fractionation zone.

* * * * *